United States Patent [19]

Cohen

[11] 4,299,235

[45] Nov. 10, 1981

[54] METHOD AND APPARATUS FOR MEASURING COST OF PHYSICAL ACTIVITY

[76] Inventor: Leonard A. Cohen, 15951 Harden Cir., Southfield, Mich. 48075

[21] Appl. No.: 78,583

[22] Filed: Sep. 21, 1979

[51] Int. Cl.³ .............................................. A61B 5/00
[52] U.S. Cl. ..................................... 128/718; 128/733
[58] Field of Search ............................... 128/670–671, 128/733, 718, 903; 364/413, 415

[56] References Cited

U.S. PATENT DOCUMENTS 3,675,640  7/1972  Gatts ................................... 128/671
4,148,303  4/1979  Cohen .................................. 128/733

OTHER PUBLICATIONS

Deroanne, R. et al., "Telemetry and Ergometry Associated to the Measurement of Oxygen Consumption during Sports Events," Conf: Int. Symp. on Biotelem., Nijmegen, Netherlands, May 5–8, 1971, pp. 101–110.

Delhez, L. et al., "Electromyographic Analysis of Respiratory Movements by Automatic Memorization during a 25 m. Underwater Dive," IBID pp. 139–150.

Primary Examiner—Robert W. Michell
Assistant Examiner—Francis J. Jaworski
Attorney, Agent, or Firm—Cushman, Darby & Cushman

[57] ABSTRACT

A method and apparatus for measuring the cost of physical activity includes the steps of correlating the integrated EMGs of selected muscles and the heart rate of an individual to oxygen consumption. Once correlated the integrated EMGs of the selected muscles and heart rate are measured while the individual is freely ambulatory. The physical and emotional cost of the physical activity is then measured. This cost is compared with the cost of the normally functioning muscles to determine the cost of a functional disability.

11 Claims, 2 Drawing Figures

METHOD AND APPARATUS FOR MEASURING COST OF PHYSICAL ACTIVITY

BACKGROUND OF THE INVENTION

A critical problem in the effective clinical evaluation of neuromuscular disabilities is how to objectively measure or quantize such disabilities. While it is relatively easy to photograph, measure or otherwise record a physical deformity or physically observe certain damage to the human body, it has proven impossible in the past to find an accurate technique for objectively measuring or quantizing the physiological cost which a disability imposes upon the use of a damaged body.

In the past, a distinction has been made between "impairment" and functional "disability". "Impairment" has been used to refer to physical limitations in the normal range of movement of a portion of the body. Relatively simple devices have been used for measuring physical restrictions in the normal action of a body due to an anatomical deformity or damage. As an example, a goniometer is typically used for determining joint angles. On the other hand, "disability" refers to a loss of normal use or functioning of a portion of the body as a result of a physical impairment. In the past, physicians have generally restricted their analysis of disabilities to measuring "impairment" and it has been left to speculation as to what the physiological costs are when a "disability" exists. Thus, subjective determination of physiological cost has typically been used by employers and/or the courts. In the absence of reliable physiological data which show objective evidence of the actual disability, there has been no accurate way of determining what the physiological cost of a disability in a human body might be.

It is accordingly an object of this invention to provide an improved method and apparatus for objectively measuring physiological disabilities in the human body.

SUMMARY OF THE INVENTION

Accordingly, this invention relates to a method and apparatus for measuring the physiological disability of a person wherein the method includes the steps of measuring the oxygen consumption, heart rate and the integrated electromyogram (hereafter EMG) for preselected muscles of a person in a clinic at a plurality of carefully controlled work levels. The EMG for selected muscles and the heart rate are then correlated to oxygen consumption. Next the heart rate and the integrated EMG of the selected muscles of the person are measured when the individual is freely ambulatory, i.e., the individual is not constrained to a particular clinic but is freely movable in his environment. The freely ambulatory integrated EMG of the person is correlated to the oxygen consumption of the individual as determined by the aforementioned clinical correlation. The freely ambulatory heart rate of the person is also correlated to the oxygen consumption as determined by the aforementioned clinical correlation. From this, the total physiological cost of the freely ambulatory activity at each work level is determined.

The physiological cost of a disability is determined by comparing the physiological cost of an impaired muscle with the physiological cost of a healthy contralateral muscle or with a population norm.

BRIEF DESCRIPTION OF THE DRAWINGS

Other objects, features and advantages to the present invention will be more fully apparent from the following detailed description of the preferred embodiment, the appended claims and the accompanying drawings in which:

DETAILED DESCRIPTION OF THE PREFERRED EMBODIMENT

Figure 1:
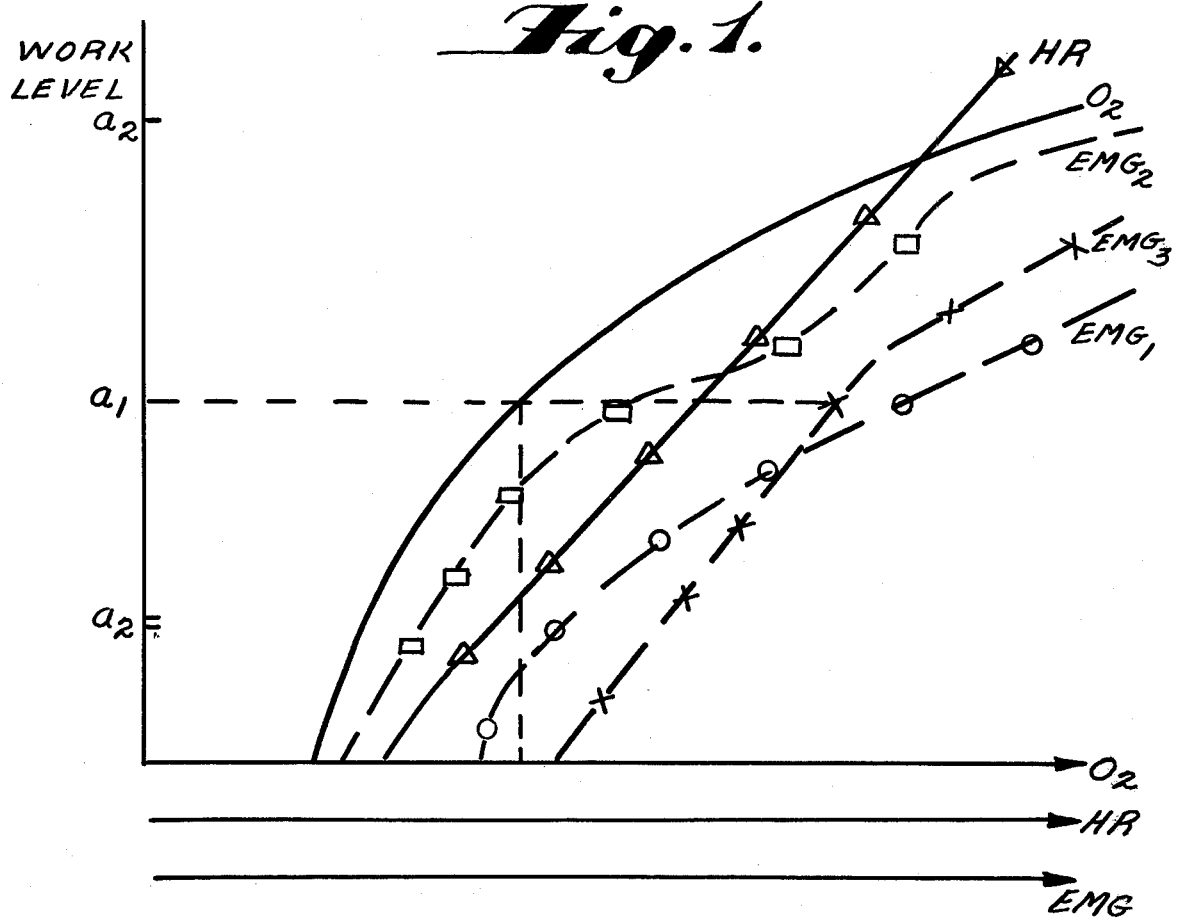
FIG. 1 is a graphical display of work with respect to selected measurable parameters of the human body.

The preferred embodiment of the invention is directed to a method of determining the physiological cost of functional disabilities in the human body. It should be understood that the physiological cost includes two primary components, namely the physiological physical cost and the physiological emotional cost. Furthermore, the term cost is used synonymously with stress and disability and each of these terms refers to the cost in energy expenditure of a functional disability. Since the only source of energy available to the body is oxidative metabolism, the measurement of oxygen consumption is a direct measure of physical energy consumed by a person. Thus, the measurement of oxygen consumption can be used to give a quantization of the physiological cost of a physical disability. In addition to physical cost of a disability, there is also an emotional cost which is manifested in increased respiratory and cardiac activity beyond physical needs. Increases in heart rate over that needed for the physical activity can be represented mathematically as excessive oxygen consumption, and, accordingly, the measurement of the increased heart rate over the normal rate for an individual gives a quantization of the emotional cost of a physical disability.

In setting up the procedure for practicing the invention, it is necessary to establish what the normal oxygen consumption levels for an individual are at different work levels. In addition, it is necessary to establish a correlation between oxygen consumption and the integrated EMG of selected muscles of an individual. To do this, a clinical work program is set up which may, for example, include walking on a treadmill, doing specific exercises or working at a desk. Different levels of work must also be established. For example, the treadmill must be operated at different but well defined inclinations. Preferably, the work type and levels should correspond to the type of activity the individual being tested will experience in normal freely ambulatory activity.

Having set up the clinical work schedule, the integrated EMG of three representative muscles of those muscles which will perform the work are taken while the patient is at rest. Typically, if a disability is suspected in one of a pair of anatomical structures, the integrated EMG of the contralateral normal muscles will be taken. If the disability is not in one of a pair of anatomical structures or is in both of such a pair, then population norms will be used as the base for comparison. In addition, the heart rate of the patient is measured during the time that the patient is at rest and by techniques known in the art, the oxygen consumption is also recorded. This can be done, for example, by using a face mask breathing system.

Next, the integrated EMG, heart rate and oxygen consumption at different work levels are recorded in the clinic. As aforementioned, the work system should reflect as close as possible the types of body movements which the patient will undergo when the patient is in a freely ambulatory environment, such as, at work or at home. Thus, for example, the normal walking routine for the patient can be simulated by means of a conventional treadmill. Tasks involving desk work can be simulated by simply positioning the patient on a bench or a chair. Preferably, several work levels should be selected which would correspond to the work levels experienced during freely ambulatory movement. Some of these selected work levels and activities may involve the use of the handicapped or disabled portions of the body structure and some may minimize their use.

After this program has been established, the work level for the individual should be monitored. As an example, assume that the treadmill is set at a certain speed and at a certain inclination. The integrated EMGs of the aforementioned three representative muscles are then measured together with the heart rate and the oxygen consumption. Each of these values is then recorded. Several samples, in the preferred embodiment, at least three, should be taken for the heart rate, oxygen consumption and EMG measurements and as soon as the measurements stabilize to within two standard deviations for the three samples the next work level is initiated. For the next work level, the same measurements are taken for at least three samples in order to achieve a second set of values for the EMG, heart rate and oxygen consumption at the second work level. This should be repeated until a reliable curve can be obtained for the patient which defines the patient's heart rate, oxygen consumption and integrated EMGs for representative muscles at any given work level. At this point, a graphical display such as illustrated in FIG. 1 will have been established for the patient which correlates the heart rate, the oxygen consumption and the integrated EMG for at least three active representative muscles with the work level.

Since the patient is to be examined in a freely ambulatory environment, the integrated EMG(s) which most closely correlates to the oxygen consumption curve must be selected. The reason for this is that oxygen cannot easily be measured when the patient is freely ambulatory since oxygen consumption measuring equipment would be required which equipment would necessarily influence the free movement of the patient. Accordingly, the integrated EMG which correlates best with the oxygen consumption curve is selected in accordance with the following guidelines:

1. The integrated EMG which is most representative of the oxygen consumption-work curve is selected;

2. If two or more integrated EMGs equally correlate to the oxygen consumption curve, they may be averaged if synergistic in action or summed if reciprocal in action or either EMG curve may be used singly;

3. If two or more integrated EMGs show different sensitivities to oxygen consumption, i.e., different variation with oxygen consumption, they may be added or, in the alternative, the most sensitive of the EMG curves used singly; and 4. If two or more integrated EMGs are proportional to oxygen consumption for only a portion of the oxygen-work curve, select those EMGs which together best cover the entire oxygen consumption range. Of course the range of EMGs values over which each given EMG is the best correlator with the oxygen consumption-work curve must be specified. In this manner, the entire range of oxygen consumption can be covered by a group of EMGs with each EMG being utilized for a certain range of work values during which that particular EMG bears the highest correlation with the oxygen consumption-work curve.

The increase of recorded oxygen consumption over the oxygen consumption at rest is depicted as a percent of the resting oxygen consumption and is called $O_2$. The corresponding heart rate increase over resting is depicted as a percent of the rest heart rate and is designated as HR. The $O_2$ and HR once calculated should be listed for each work level. These two quantities have a relationship to the normal physiological cost including both the physical and emotional components for normal performance of the patient at each of the respective work levels.

The physical cost is proportional to the work done and can be computed by the following formula:

$$PC_{al} = K(O_{2al} - O_{2r})/O_{2r} \tag{1}$$

Where $PC_{al}$ is the physical cost of a type of work designated (a) at the first work level, $O_{2al}$ is the oxygen consumption of work type (a) at the first level, and $O_{2r}$ is the oxygen consumption at rest, and K is a constant.

The emotional component of the physiological cost is proportional to the heart rate and can be computed by the following formula:

$$EC_{al} = 100(HRO_2 - O_{2al})/O_{2r} \tag{2}$$

Where $EC_{al}$ is the emotional component of the physiological cost for task or work type (a) at the first level and $HRO_2$ is the actual heart rate converted to oxygen consumption from the curve illustrated in FIG. 1 which shows the oxygen consumption corresponding to the heart rate at the first level of work (a). The total physiological cost can be computed by summing PC and EC.

After these calculations have been made, the patient is instrumented for testing in a freely ambulatory environment. This is done by instrumenting the patient with integrated EMG recorders for the relevant muscles to be measured and instrumenting the patient for measuring the patient heart rate. The patient is then sent out to perform in his normal environment. The patient performs work in accordance with his or her normal routine and the heart rate together with the integrated EMG data are recorded. The recording should be plotted and the integrated EMG curve or curves which best correlate to the originally plotted oxygen consumption curve selected. These integrated EMG curves will represent the physical work performed at each representative physical work level and task. Thus, work in watts corresponding to the oxygen consumption and integrated EMG values will be among the simultaneous curves plotted. The ambulatory integrated EMG recorded at any point, for example, at any given work level of interest, becomes the reference point from which an abscissa is drawn to intersect the oxygen consumption curve. The abscissa intersection with the oxygen consumption curve will specify the oxygen consumption level which corresponds to the EMG in integrated EMG units.

For example, if the ambulatory integrated EMG of the most representative muscle is 2439, select the 2439 point on the integrated EMG curve for the same muscle which was obtained under controlled conditions as set forth hereinabove. Read from the curve obtained under controlled conditions, the oxygen consumption and work in watts where the abscissa of the point 2439 crosses the oxygen consumption curve and the work curves. In this manner, the oxygen consumption representing the physical cost of the work can be obtained in a freely ambulatory patient for each EMG work level selected.

There is no feasible oxygen consumption recording system in existence for freely ambulatory patients which is lightweight enough so as not to introduce a significant physical and emotional factor of its own causation. Accordingly, this lack of ability to obtain oxygen consumption values presents a serious obstacle to meaningful physiological measurements of physical work in the human body. Accordingly, the present invention which makes use of integrated EMG and heart rate values provides an easy means for computing the physical cost as well as emotional cost of a disability impairment.

In computing the physiological cost of an impairment, it is to be emphasized that of the parameters measured the integrated EMG represents the physical work as opposed to emotional work in much the same manner as oxygen consumption correlates with physical work. The heart rate data provide an indication of the emotional work. Furthermore, clinically derived curves for a given patient not only yield an oxygen consumption value, but generate one of maximum accuracy greatly exceeding the accuracy if a population average curve were used in place thereof. With the aforementioned data established, the oxygen consumption value representing physical cost of activity can be derived from the recorded, integrated EMG values using a family of curves previously obtained from the patient in the clinic. These values can be substituted to solve the following equation:

$$PC_{al} = (EMGO_2 - O_{2r})/O_{2r} \qquad (3)$$

Where $PC_{al}$ represents the physical cost of activity "a" at level "1", $EMGO_2$ is the recorded free ranging EMG value converted to the $O_2$ consumption for clinically obtained curves and $O_{2r}$ is the directly recorded oxygen consumption at rest obtained from the patient in the clinic.

The emotional cost of activity can be derived from the recorded integrated values using the family of curves previously obtained from the patient in the clinic. Thus, values can be substituted to solve the following equation:

$$EC_{al} = (HRO_2 - EMGO_2)/O_{2r} \qquad (4)$$

Where $EC_{al}$ is the emotional cost of an activity "a" at level "1", $HRO_2$ is the recorded heart rate converted to oxygen consumption from the curves obtained from the same patient in the clinic and $EMGO_2$ is the recorded free-ranging EMG value converted to oxygen consumption from the clinically obtained curves. The total physiological cost is given by the following formula:

$$C_{al} = PC_{al} + EC_{al} \qquad (5)$$

These calculations can be repeated for as many different types and levels of activity as desired from the recorded records of the freely ambulatory patient or from his diary. Thus, the physiological cost of performing with an alleged disability can be objectively and quantitatively measured and, moreover, the physical cost and emotional cost which together constitute the physiological cost can be separately measured in an objective and quantitative manner from data obtained from a free-ranging patient going about his normal activities in his normal environment.

In the preferred embodiment, a small recorder typically weighing only about $1\frac{1}{2}$ pounds is the only item that can be seen on the body of the patient and this is only viewed as a type of small radio, that is, it can be worn on a waist belt. Accordingly, the recording system is physically as well as cosmetically of no consequence to the patient and, accordingly, poses no significant alteration of normal patient activity.

In order to determine whether a patient has been physically impaired by a disability the physiological cost of an activity should be related to the mean physiological cost of normal organisms while performing the same activity. The standard for statistically meaningful deviation from the mean is two standard deviations. Thus, any value falling within plus or minus 2 standard deviations of the mean is within 95% of the population making up the mean. Accordingly, if the value of the physiological cost for a given type and level of task is greater than plus or minus 2 standard deviations of the mean, it is statistically sound and reasonable to conclude that the individual or patient is outside of the normal population and is therefore part of a statistically different population. Thus, such a statistically validated abnormal person may be entitled, for example, to vocational rehabilitation or monetary compensation for his functional disability in proportion to the earning power of the impaired function. This simply means that the patient must pay an abnormally high physiological cost to perform a given task in comparison to normal people. In this connection, it should be understood that in some activities, the physical cost may be negligible or nonexistent whereas pain suffered in performing an activity may be real and be something which should be compensated for. Thus, the pain manifests itself in a relatively high emotional cost for the disability. Furthermore, if the emotional cost computed from the aforementioned technique is significantly elevated but not normally correlated with the use of the affected muscle or structure, the patient feels pain in much the same manner as a patient may erroneously believe he has a physical disability even though his physical cost for an activity is normal. Thus, emotional problems and pain can be also identified and objectively measured and accordingly each can be effectively addressed both on a medical and on a legal basis.

Figure 2:
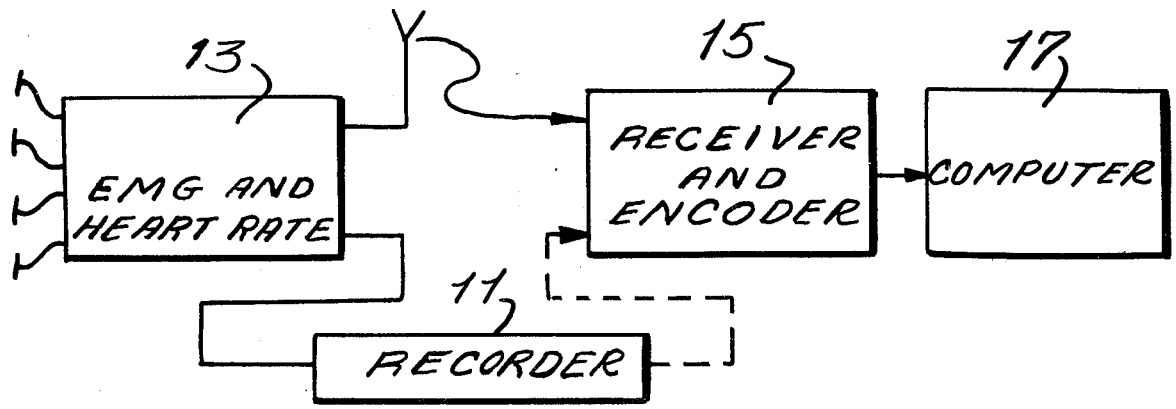
FIG. 2 is a block diagram of a preferred test system.

In the preferred embodiment, the apparatus includes a recorder which is positioned on the body of the patient. The recorder includes electrodes for attachment to the body to measure the integrated EMGs and the heart rate. This is illustrated by the recorder 11 of the FIG. 2 which receives the output of a conventional EMG and heart rate measuring device 13.

The output of the recorder 11 is then inputted to a receiver and encoder 15 which converts the information to computer readable form in a manner well-known in the art. The output is coupled to the computer 17 which preferably can be any suitable digital computer or minicomputer. The computer, in accordance with the aforementioned method, correlates the freely ambulatory heart rate and integrated EMG measurements to the oxygen consumption and then computes the physical as well as emotional cost of an activity. Preferably, the computer provides a printout of the physical and emotional cost of various levels of activity.

While the present invention has been disclosed in connection with the preferred embodiment thereof, it should be understood that there may be other embodiments that fall within the spirit and scope of the invention as defined by the following claims.

What is claimed is:

1. A method of measuring the cost of physical activity of a person comprising the steps of:
   measuring the consumption of oxygen while at rest;
   measuring the consumption of oxygen and the integrated electromyogram of at least one muscle while in a controlled state of activity;
   correlating said at least one electromyogram to said oxygen consumption;
   measuring the integrated electromyogram of said at least one muscle while said person is freely ambulatory;
   correlating said integrated electromyogram to said oxygen consumption; and
   determining the change in consumption of oxygen for said freely ambulatory activity.

2. The method of claim 1 further comprising the steps of:
   measuring the heart rate while in said controlled state of activity;
   correlating the heart rate while in said controlled state of activity to said oxygen consumption;
   measuring the heart rate of said person while freely ambulatory;
   correlating said measured heart rate while freely ambulatory to said oxygen consumption; and
   determining the difference between the oxygen consumption correlated to said at least one electromyogram and the oxygen consumption correlated to said heart rate.

3. A method of measuring the physiological disability of a person comprising the steps of:
   measuring the energy consumed by said person when at rest;
   measuring the integrated electromyogram of at least one selected muscle;
   correlating the integrated electromyogram of said at least one selected muscle with the energy consumed by said person in a controlled state of activity;
   measuring the integrated electromyogram of said at least one muscle of said person while said person is freely ambulatory; and
   determining from said measured consumption of energy at rest and from said measured integrated electromyogram, the physical cost of said freely ambulatory activity.

4. A method of measuring the physiological disability of a person comprising the steps of:
   measuring the energy consumed by said person when at rest;
   measuring the integrated electromyogram of at least one selected muscle;
   correlating the integrated electromyogram of said at least one selected muscle with the energy consumed by said person in a controlled state of activity;
   measuring the integrated electromyogram of said at least one muscle of said person while said person is freely ambulatory;
   determining from said measured consumption of energy at rest and from said measured integrated electromyogram, the physical cost of said freely ambulatory activity;
   correlating the heart rate of said person to the energy consumed by said person while in said controlled state of activity;
   measuring the heart rate of said person when freely ambulatory;
   determining the emotional cost of said freely ambulatory activity from said measured heart rate, said consumption of energy at rest and said integrated electromyogram; and
   determining the physiological disability of said person by summing said physical cost and said emotional cost of said freely ambulatory activity.

5. A method of measuring the cost of physical activity of a person comprising the steps of:
   measuring a parameter having a high correlation to physical energy consumption in a person while said person is in a controlled state of activity;
   measuring a second parameter of said person having a high correlation to said first parameter while said person is in said controlled state of activity, said second parameter having a low correlation to emotional energy consumption in both the controlled and freely ambulatory states of activity;
   correlating the measurements of said second parameter to said first parameter;
   measuring said second parameter while said person is freely ambulatory; and
   determining from said measured first parameter and said measured second parameter the physical cost of said freely ambulatory activity.

6. A method of measuring the cost of freely ambulatory activity of a person comprising the steps of:
   measuring oxygen consumption of said person while at rest, said oxygen consumption having a high correlation to energy consumption;
   measuring the electromyogram of a least one muscle of said person, said electromyogram having a correlation to said oxygen consumption, said measurement of said integrated electromyogram being taken while in a controlled state of activity;
   correlating said measured integrated electromyogram to said oxygen consumption;
   measuring said integrated electromyogram while said person is freely ambulatory; and
   determining from said measured oxygen consumption and said integrated electromyogram the physical cost of said freely ambulatory activity.

7. The method of claim 6 further comprising the steps of:
   measuring the heart rate while said person is in said controlled state of activity;
   correlating said measured heart rate to said oxygen consumption;
   measuring said heart rate while in a freely ambulatory state; and
   determining from said oxygen consumption, said heart rate and said electromyogram, the emotional cost of said freely ambulatory activity.

8. The method of claim 7 further comprising the step of:
   measuring the oxygen consumption while said person is in said controlled state of activity.

9. A method of measuring the physiological state of activity of a person comprising the steps of:

measuring a parameter having a high correlation to physical energy consumption in a person while said person is in a controlled state of activity;

measuring a second parameter of said person having a high correlation to said first parameter while said person is in said controlled state of activity, said second parameter having a low correlation to emotional energy consumption in both the controlled and freely ambulatory states of activity;

measuring a third parameter having a correlation to total physiological activity and to said first parameter of said person while said person is in said controlled state of activity;

correlating said second and third parameters to said first parameter and to a selected common unit of measurement;

measuring said second and third parameters while said person is freely ambulatory; and subtracting the correlated measured value of said second parameter from the correlated measured value of said third parameter to determine the emotional cost of activity.

10. The method of claim 9 wherein said first parameter is oxygen consumption, said second parameter is the integrated electromyogram and said third parameter is the heart rate.

11. A method of measuring the cost of physiological activity of a person comprising the steps of:

measuring a parameter having a high correlation to physical energy consumption in a person while said person is in a controlled state of activity;

measuring a second parameter of said person having a high correlation to said first parameter while said person is in said controlled state of activity, said second parameter having a low correlation to emotional energy consumption in both the controlled and freely ambulatory states of activity;

measuring a third parameter having a correlation to the total physiological cost of activity while said person is in a controlled state of activity;

correlating said second and third parameters to a common unit of measurement with said first parameter;

measuring said second and third parameters while said person is freely ambulatory; and determining from said measuring first, second and third parameters the total physiological cost of said freely ambulatory activity.

* * * * *